(12) United States Patent
Baum et al.

(10) Patent No.: US 9,247,867 B2
(45) Date of Patent: Feb. 2, 2016

(54) ENDOSCOPIC ARRANGEMENT (75) Inventors: Eckhart Baum, Duerbheim (DE);
Klaus-Martin Irion,
Emmingen-Liptingen (DE); Peter Schwarz, Tuttlingen-Nendingen (DE);
Daniel Efinger, Aldingen (DE)

(73) Assignee: Karl Storz GmbH & Co. KG,
Tuttlingen (DE)

( * ) Notice: Subject to any disclaimer, the term of this patent is extended or adjusted under 35 U.S.C. 154(b) by 27 days.

(21) Appl. No.: 13/541,269

(22) Filed: Jul. 3, 2012

(65) Prior Publication Data
US 2013/0012777 A1 Jan. 10, 2013

(30) Foreign Application Priority Data

Jul. 4, 2011 (DE) .......................... 10 2011 106 386

(51) Int. Cl.
| | |
|---|---|
| A61B 1/04 | (2006.01) |
| A61B 1/06 | (2006.01) |
| A61B 1/00 | (2006.01) |
| A61B 1/05 | (2006.01) |
| H04B 10/80 | (2013.01) |
| H04B 10/25 | (2013.01) |

(52) U.S. Cl.
CPC ........... *A61B 1/0653* (2013.01); *A61B 1/00013* (2013.01); *A61B 1/00029* (2013.01); *A61B 1/00126* (2013.01); *A61B 1/00165* (2013.01); *A61B 1/051* (2013.01); *H04B 10/25* (2013.01); *H04B 10/807* (2013.01); *A61B 1/0002* (2013.01); *A61B 1/00016* (2013.01); *A61B 1/0017* (2013.01); *A61B 1/041* (2013.01)

(58) Field of Classification Search
CPC ........... A61B 1/00011; A61B 1/00013; A61B 1/00004; A61B 1/00006; A61B 1/00009
USPC .......... 600/109, 110, 112, 132, 136, 137, 182
See application file for complete search history.

(56) References Cited

U.S. PATENT DOCUMENTS

| | | | |
|---|---|---|---|
| 4,679,448 A | 7/1987 | Lund | |
| 5,902,230 A * | 5/1999 | Takahashi et al. | ............ 600/109 |
| 6,458,078 B1 | 10/2002 | Ludtke et al. | |

(Continued)

FOREIGN PATENT DOCUMENTS

| | | |
|---|---|---|
| DE | 19604257 A1 | 8/1996 |
| DE | 19947811 A1 | 5/2001 |

(Continued)

*Primary Examiner* — Anhtuan T Nguyen
*Assistant Examiner* — William Chou
(74) *Attorney, Agent, or Firm* — Whitmyer IP Group LLC (57) ABSTRACT Endoscopic arrangement comprising a first distal end, an imaging device arranged at the first distal end, a first proximal end for connection to a supply unit, a data transmission element embodied as a light guide and having a second distal end and a second proximal end, and comprising an electro-optical converter, wherein the electro-optical converter is configured to convert digital data generated by the imaging device into an optical signal, wherein the data transmission element at its second distal end is optically coupled to the electro-optical converter for coupling the optical signal into the data transmission element, wherein the imaging device comprises at least two data outputs each having a digital output signal, and wherein a first signal converter is provided between the imaging device and the electro-optical converter for combining the digital output signals into a digital combined output signal.

21 Claims, 6 Drawing Sheets

(56) References Cited

U.S. PATENT DOCUMENTS

| | | | |
|---|---|---|---|
| 6,466,256 B1 | 10/2002 | Takahashi et al. | |
| 7,196,391 B2 * | 3/2007 | Hsieh | H01L 27/14609 257/291 |
| 8,622,893 B2 * | 1/2014 | Mathieu | 600/132 |
| 2001/0038451 A1 * | 11/2001 | Jung et al. | 356/328 |
| 2001/0051766 A1 * | 12/2001 | Gazdzinski | 600/309 |
| 2006/0069307 A1 * | 3/2006 | Boulais | 600/132 |
| 2007/0232860 A1 * | 10/2007 | Kubo et al. | 600/160 |
| 2008/0039686 A1 | 2/2008 | Mori et al. | |
| 2010/0069721 A1 * | 3/2010 | Webler et al. | 600/182 |
| 2010/0198009 A1 * | 8/2010 | Farr et al. | 600/109 |

FOREIGN PATENT DOCUMENTS

| | | |
|---|---|---|
| JP | 2006051162 A | 2/2006 |
| JP | 2006181021 A | 7/2006 |

\* cited by examiner

Fig. 8 ular applications video-assisted endoscopic units are also used in various technical fields of application, e.g. pipe inspection, engine inspection or motor inspection, etc.

ENDOSCOPIC ARRANGEMENT

CROSS-REFERENCES TO RELATED APPLICATIONS

This application claims priority from German patent application DE 10 2011 106 386.6, filed on Jul. 4, 2011. The entire contents of this priority application is incorporated herein by reference.

BACKGROUND OF THE INVENTION

The present invention relates to an endoscopic arrangement comprising a first distal end at which an imaging device is arranged, and comprising a first proximal end for connection to an electrical unit, comprising a data transmission element embodied as a light guide and comprising a second distal end and a second proximal end, and comprising an electro-optical converter which is configured to convert digital data provided by the imaging device into an optical system, and wherein the data transmission element is optically coupled at its second distal end to the electro-optical converter for coupling the optical signal into the data transmission element.

U.S. Pat. No. 6,458,078 B1 shows an endoscope fitted with an electric system and a light guide.

SUMMARY OF THE INVENTION

For endoscopic arrangements, in particular for endoscopes and video-assisted endoscopic units, there is a constant need for systems having an improved resolution, in particular a high resolution, and which offer color fidelity. This includes endoscopic cameras, which are often coupled to rigid endoscopes at the proximal side. However, as will be explained later, the invention is also directed at video endoscopes which carry the imaging devices in their tip and which are often flexible. Further, endoscopic capsules are accounted for which autonomously pass through the gastrointestinal tract transmitting image information. In the context of endoscopic capsules the transmission takes place wirelessly. Sometimes endoscopic capsules have been provided with a recording medium for a later review of the image information. In addition to the medical applications video-assisted endoscopic units are also used in various technical fields of application, e.g. pipe inspection, engine inspection or motor inspection, etc.

Despite various efforts according to the prior art in the context of imaging sensors with high or very high resolution in the context of image transmission when using small diameters in combination with endoscopic transmission lengths, which vary according to the endoscopic application, a number of problems still exist. In particular for endoscopic cameras and video endoscopes there is a need for transmission systems with a small diameter and little weight, including the cable, which offer a wide range of possible cable lengths. At this point, no video endoscope is known having a small diameter and a so called full-HD-resolution in the range of about two million pixels. There are endoscopic cameras having a full-HD-resolution, however, the diameter of the cable is relatively large and the cable is somewhat heavy so that the endo-surgical handling is somewhat cumbersome.

The situation is particularly troublesome with endoscopic capsules which according to the current state can only offer an inferior image resolution and only an inferior image frequency. One of the reasons is that a wireless transmission at higher bandwidths through human tissue is not possible. If an endoscopic capsule is provided with memory, even the memory media available today will exhaust the capacity of the memory and the available space very quickly, if it is desired to store a full-HD-video at an image frequency of 25 Hz or 30 Hz.

Endoscopic arrangements having an electronic imaging system at their distal side or at their proximal side are using complicated and expensive cabling systems according to the prior art in order to transmit the image information from the endoscope to a control unit which is located remote from the patient as well as to transmit control information and electrical energy from the control unit to the imaging system. The goal of improving the image resolution intends to provide the surgeon a preferably natural endoscopic image at high resolution for the surgery. The immediate consequence stemming from the higher number of pixels in the imaging sensors are always increasing signal transmission frequencies. In order to reduce the signal dampening at higher transmission frequencies and to increase the effective bandwidth larger cable diameters are required. In addition to the increase in weight the electromagnetic compatibility (EMC) poses a more significant problem.

In addition, there is the problem for video endoscopes that an increase of the cable diameter is hardly possible, since this would increase the overall diameter or would reduce the diameter of other mandatory endoscopic components as suction channels, fiber optic cables, etc.

A further requirement directed at endoscopic cameras and at video endoscopes is that the cable systems at the endoscope or at the camera at the proximal side must have a collection that is easily separable for cleaning and sterilization purposes. Since the imaging systems are used often the cable systems are regarded as consumables and must offer an easy repair or replacement. As the systems have a complex structure with multiple cores, the cable system along with its connections represents a significant part of the costs of the total system. Therefore, it is a further goal to reduce the manufacturing costs of the cable system.

It is an object of the present invention to provide an improved endoscopic arrangement which offers a small diameter of the transmission system, small losses due to dampening and high transmission frequencies and allows large cable lengths of 16 ft. and more at small weight and favorable costs. It is an object that the endoscopic arrangement has a small electromagnetic emission and can be applied in the context of endoscopic cameras, video endoscopes and endoscopic capsules.

There is provided an endoscopic arrangement as described before wherein the imaging device comprises at least two data outputs each having a digital output signal and wherein a first signal converter is arranged between the imaging device and the electro-optical converter, wherein the signal converter is configured to combine the digital output signals into a digital combined output signal.

One feature of the invention is that digital data of at least two data outputs can be transmitted almost simultaneously without requiring multiple parallel lines. In order to achieve this, the digital output signals arrive in a parallel arrangement at the signal converter and are subsequently combined into a digital combined output signal. In a preferred refinement the digital output signals are serialized via a multiplexer.

The output signals of the imaging device shall be understood as serial signals. If a data output comprises parallel output signals which transmit image data, the individual signals of the parallel signals are each understood again as a serial signal. According to a preferred refinement the expression "parallel" is to be understood in that a plurality of output signals can concurrently transmit useful data comprising image information.

The imaging device is an image capturing device with at least two data outputs, preferably with outputs for data and timing information, or comprises at least two image capturing devices each having at least one data output, preferably an output with a combined data/clock-signal. The first option can be represented by an imaging sensor having an imaging surface wherein for reading the image data the imaging surface is divided into at least two partial areas, each of their information sent via a separate data output having a combined data/clock-signal. Also, there may be an imaging sensor having a first data output having a data signal only and a second data output having a clock signal. For the second option there may preferably be at least two imaging sensors having separate imaging surfaces, wherein each imaging sensor has at least one data output with a combined data/clock-signal.

The electro-optical converter and the signal converter can each be embodied as discrete elements, however, preferably they are combined in one device. Preferably, the electro-optical converter is embodied as a laser diode, in particular as a VCSEL-diode (vertical-cavity surface-emitting laser). Preferably, exactly one laser diode or a maximum of two laser diodes are used if it is desired to keep the required space small.

The imaging device preferably comprises an objective, or an objective is preferably associated with the imaging device. The configuration of the electro-optical converter and the signal converter is preferably such that signals can be sent and transmitted bidirectionally away from the imaging device and to the imaging device. This allows in a simple manner to use the data transmission element at the same time for transmitting control signals into the direction of the imaging device. Preferably, it is also possible to use an opto-electrical converter at the distal end for coupling out control signals at the first distal end. Preferably, the wave length of the light generated by the electro-optical converter lies between 700 nm and 1550 nm.

In general, any signal originating at the imaging sensor and comprising imaging data is to be understood as an output signal or as a data signal. However, the output signal does not have to be limited to imaging data only, but may also comprise timing information or other data which describe the imaging data. It is deemed preferable if the data outputs of the image capturing device are each configured differentially. The resulting parallel differential signals can then be combined before the electro-optical converter or in the electro-optical converter or can be viewed as parallel output signals which are combined in the digital combined output signal by the signal converter.

The disclosure may enable a number of advantages, including a small size at the distal side and a very small diameter of the data transmission element at a high data rate, preferably of more than 1 Gbit/s. Further, problems related to EMC along the length of the cable may be avoided. In comparison, electrical cores behave like antennas, wherein a shielding can be very difficult due to the problems regarding diameter and the available space. In using the electro-optical coupling a galvanic separation is provided which is preferable according to some regulations for medical endoscopic systems. A further advantage may be available in that the system due to its short electrical cores and the optical transmission may be suitable for an application in MR-systems (magnetic resonance systems) at least regarding the desired transmission of information at high resolution.

Regarding the first signal converter it may be preferred that it comprises a coder and a multiplexer which generates a combined digital output signal at a higher clock rate and without a constant component based on the multiple digital output signals of the imaging unit. In this context it is preferred to use a 8B/10B-coding where each 8-bit-word is assigned a 10-bit-word in order to achieve a suppression of a constant component. Preferably, the multiplexer uses a time multiplexing method, wherein it is possible to apply at least one of a synchronous and an asynchronous mode.

Preferably, the electrical unit may be a supply unit or a camera control unit supplying the distal electronics with electrical energy, controlling the imaging device and processing the image information.

According to a refinement the signal converter comprises a buffer memory configured to temporarily store at least one of the digital output signals, and preferably all digital output signals.

This refinement may allow for a very good flexibility with regard to the processing of multiple output signals. Preferably it may be possible that the data rate of the transmission via the data transmission element is higher, more preferably significantly higher and in particular at least twice the data rate of one of the output signals from one of the data outputs of the imaging device. It is preferred that the buffer memory has a size for buffering the information corresponding to at least one image pixel, more preferably to at least a row of pixels and even more preferably to at least one full image as can be provided by the corresponding data output. This may allow for generating the digital combined output signals in a pixel-wise, row-wise or image-wise manner. Since the data transmission element allows for very high data rates it may become possible to transmit, for example, the image information of four imaging areas at four times the data rate via the data transmission element almost simultaneously.

In a refinement the imaging device has a video resolution of more than 0.75 megapixel, preferably of more than 1.5 megapixel, more preferably of more than 2 megapixel and in particular of more than 3 megapixel.

This refinement is advantageous since it is possible to easily transfer large amounts of image data via the endoscopic arrangement. The term "video resolution" is understood, according to a further refinement, as a resolution at which at least 15 images per second, preferably at least 25 images per second and more preferably at least 30 images per second are transmitted.

According to a further refinement there is provided a first opto-electrical converter at the second proximal end of the data transmission element, the converter configured to couple the optical signal out of the data transmission element and to convert the optical signal into digital data, wherein a second signal converter is connected to the first opto-electrical converter which is configured to separate one digital combined output signal into at least two digital output signals.

This refinement may allow for an easy recovery of the original signals which the first signal converter has been provided with. The fact that the signal at the proximal side is also called a digital combined output signal is to be understood in the sense that even if the signal is not the same physical signal due to the electro-optical and opto-electrical conversions, it still contains the same information as the digital combined output signal at the distal side. Preferably, the second signal converter is embodied as a demultiplexer.

In a refinement a spectral divider is arranged between the electro-optical converter and the second distal end of the data transmission element.

This refinement may allow in an easy manner to use the data transmission element bidirectionally. If light, preferably visible light, is coupled from the proximal side into the data transmission element, it may be separated via the spectral divider at the distal side from that light that is sent from the electro-optical converter for the transmission of information. The spectral divider may preferably be used effectively if there is a sufficient separation of the wave length for the transmission of information and the wave length for the transmission of visible light. To do so, the upper limit of the wave length for visible light, according to a refinement, is at 650 nm, preferably at 550 nm and more preferably at 500 nm. The lower limit of the wave length for the transmission of information, according to a refinement, is at 700 nm, preferably at 900 nm and more preferably at 1100 nm. The bidirectional transmission allows for two uses without increasing the diameter of the transmission medium. Preferably, for a spectrally separated transmission of light in the visible range and information in an infrared range, in particular in a near-infrared range, multimode-fibers are used.

In a further refinement a second opto-electrical converter is arranged at the first distal end of the endoscopic arrangement which is configured to convert light into electrical energy which is coupled into the data transmission element at the proximal side.

This refinement may offer the advantage of using the data transmission element bidirectionally and to provide electrical energy at the distal side under galvanic separation, preferably for supplying the imaging device. In order to achieve this, the energy, which is at least partially to be provided to the first distal end of the endoscopic arrangement, is input into the data transmission element at the proximal side. At the first distal end of the endoscopic arrangement the light is preferably coupled out via a spectral divider. The light intended for the supply of energy is directed to the opto-electrical converter which is preferably embodied as a solar cell.

In a further refinement, an exit for visible light and a luminescence converter are arranged at the first distal end of the endoscopic arrangement wherein the luminescence converter is configured to convert light that is guided in the data transmission element in the direction of the distal side into white light and to guide it to the exit.

This refinement offers to provide light, which is input at the proximal side, as white light and achieves at the same time a good spectral separation between this light and the light used for the transmission of information. As has been explained the separation of the light for lighting purposes and the light for the transmission of information can be achieved well if there is a sufficient separation between the wave lengths used. This means, however, that the light for lighting purposes is preferably in the blue to violet range and thus has a color which is unsuitable for endoscopic observations. By feeding light to a luminescence converter, which is preferably embodied as a fluorescence converter or a phosphorescence converter, white light, at least light similar to white light, is obtained from the blue/violet light. This light is suitable for lighting purposes.

In a refinement, a light source is provided at the proximal end of the endoscopic arrangement, wherein the light source is configured to couple light at the first proximal end into the data transmission element.

This refinement offers the possibility to use the data transmission element for an additional possibility of providing lighting and/or for obtaining electrical energy at the first distal end of the endoscopic arrangement. The wave length of the light that is emitted from the light source is preferably between 380 nm and 490 nm, more preferably between 390 nm and 430 nm. Preferably, the data transmission element is embodied as a multimode-fiber.

In a further refinement the data transmission element is provided with a separation section at the first proximal end of the endoscopic arrangement which is configured to allow for separating and/or rotatably coupling the endoscopic arrangement from/to a electrical unit at the proximal side.

This refinement may allow for an easy replacement of the endoscopic arrangement. If the separation section is arranged in the data transmission element, the separation section can be preferably realized if the transmission elements within the data transmission element are configured coaxially. This may allow for a rotation of the endoscopic arrangement relative to the electrical unit at the proximal side. This may allow for a particularly well handling.

In an further refinement the data transmission element comprises a monomode-fiber.

This refinement may allow for a very small diameter of the data transmission element. The fiber core of a monomode-fiber has usually less than 10 μm. Further monomode-fibers have a small dampening. A wave length for the transmission of 1550 nm±200 nm, preferably 1550 nm±100 nm and more preferably 1550 nm±50 nm is currently considered preferable. The endoscopic arrangement then allows for minimal diameter dimensions for the endoscopic capturing and transmission of HD-images which could previously not be realized. The light guide has preferably a diameter of less than 4 mil (0.1 mm).

In a refinement the imaging device is configured to transmit the output signals according to the MIPI D-PHY or MIPI M-PHY specification.

This refinement uses a device-internal serial standard transmission format from the mobile communication sector which, however, can only be used for short cable lengths of less than 1 ft (30 cm) and is thus unknown in the field of endoscopy. Since the disclosed endoscopic arrangement requires electrical cores, especially conductors, only to the first signal converter or to the first electro-optical converter, respectively, and since the greatest part of the transmission path takes place over the data transmission element which is embodied as a light guide and thus takes place almost without any dampening, this standard can now be used advantageously in the field of endoscopy. Due to the optical transmission the transmission lengths can be varied in a wide range and far beyond the limit of 1 ft (30 cm) without a significant change in the high-frequency signal, e.g. due to dampening. The use of this standard further allows to use a number of cost-efficient imaging sensors. The use of expensive proprietary imaging sensors thus may be avoided. It is noted that the specification MIPI M-PHY is a standard that is becoming more popular and which is to become widely recognized in the field of mobile communications.

In a further refinement the first signal converter is configured to couple the digital combined output signal into at least two fibers of the data transmission element.

This may provide a very good reliability of the endoscopic arrangement. If one of the fibers of the data transmission element has a defect, the complete transmission of the image information is continuously ensured via the remaining fiber or fibers. If the opto-electrical converter at the proximal side and/or the second signal converter are configured to verify the functionality of the fibers of the data transmission element and to detect a failure of a fiber, the surgeon can be given an indication for a necessary repair or replacement without having to interrupt the current procedure.

In a further refinement the opto-electrical converter and/or the second signal converter can be coupled to the electrical unit via an electrical connector.

This refinement may allow for a cost-efficient replacement of the endoscopic arrangement. Endoscopic arrangements, as explained, will typically be flexible or rigid video endoscopes or video catheters which carry an imaging unit in their distal section. However, there may also be endoscopic cameras which may be coupled to conventional endoscopes and which may be designed small and light-weight in their distal section.

In a further refinement the endoscopic arrangement is part of an endoscopic capsule, wherein the capsule comprises a capsule body in which the distal elements of the endoscopic arrangement are enclosed, and comprising an insertion system.

Such an endoscopic capsule may have a small size and may provide a high image quality.

In a further refinement the endoscopic arrangement is part of an endoscopic capsule, wherein the data transmission element is wound at the proximal side as a roll on a roller.

This refinement may allow for an easy application of the endoscopic capsule without the risk of the data transmission element becoming tangled up. As previously explained, the data transmission element may have a diameter of less than 0.4 in (1 mm) and may be used, in addition to the signal transmission, simultaneously for supplying light and energy, a very suitable, and perhaps even optimal, connecting element which does not impede the movement of the capsule in the gastrointestinal tract.

In a further refinement the endoscopic arrangement is part of an endoscopic video camera for the inspection of hollow organs or cavities. The data transmission element is preferably embodied as a hybrid cable which comprises the light guides for the data transmission as well as the electrical cores for the power supply and for low-frequency control signals.

In a further refinement the endoscopic arrangement is part of a video endoscope, wherein the data transmission element comprises a connector system which allows for a separation, e.g. of the optical signal line at a handle of the endoscope or at the distal side near the imaging sensor or at the proximal side at a fiber optic connector, e.g. for cleaning purposes.

In a further refinement the endoscopic arrangement is releasably coupled to an endoscope body.

In a further refinement the endoscopic arrangement is part of a laryngoscope, preferably of a disposable laryngoscope, wherein the data transmission element leads into the handle of the laryngoscope. There, in addition to the opto-electrical converter and the second signal converter, a data compressor and a wireless transmitter (e.g. WIFI, WHDI, WirelessHD, UWB, WiGig, etc.) which allows for a wireless communication of the image data to the supply unit or to a display, are integrated.

In a further refinement the endoscopic arrangement is integrated into a rigid or flexible endoscope, wherein the data transmission element leads into a proximal handle of an endoscope and wherein an optical converter, a data compressor and a wireless transmitter (e.g. WIFI) are arranged in the handle of the endoscope.

In a refinement the endoscopic arrangement is part of an endoscopic capsule for inspection of the gastrointestinal tract or other hollow organs or cavities, wherein the capsule comprises a battery for the distal power supply of the electrical components.

BRIEF DESCRIPTION OF THE DRAWINGS

It is appreciated that the features explained above and the features that will be explained below may be applied alone or in any combination without departing from the spirit and scope of the invention.

Embodiments are shown in the Figures and will be explained in the following. There is shown.

DESCRIPTION OF PREFERRED EMBODIMENTS

Figure 1:
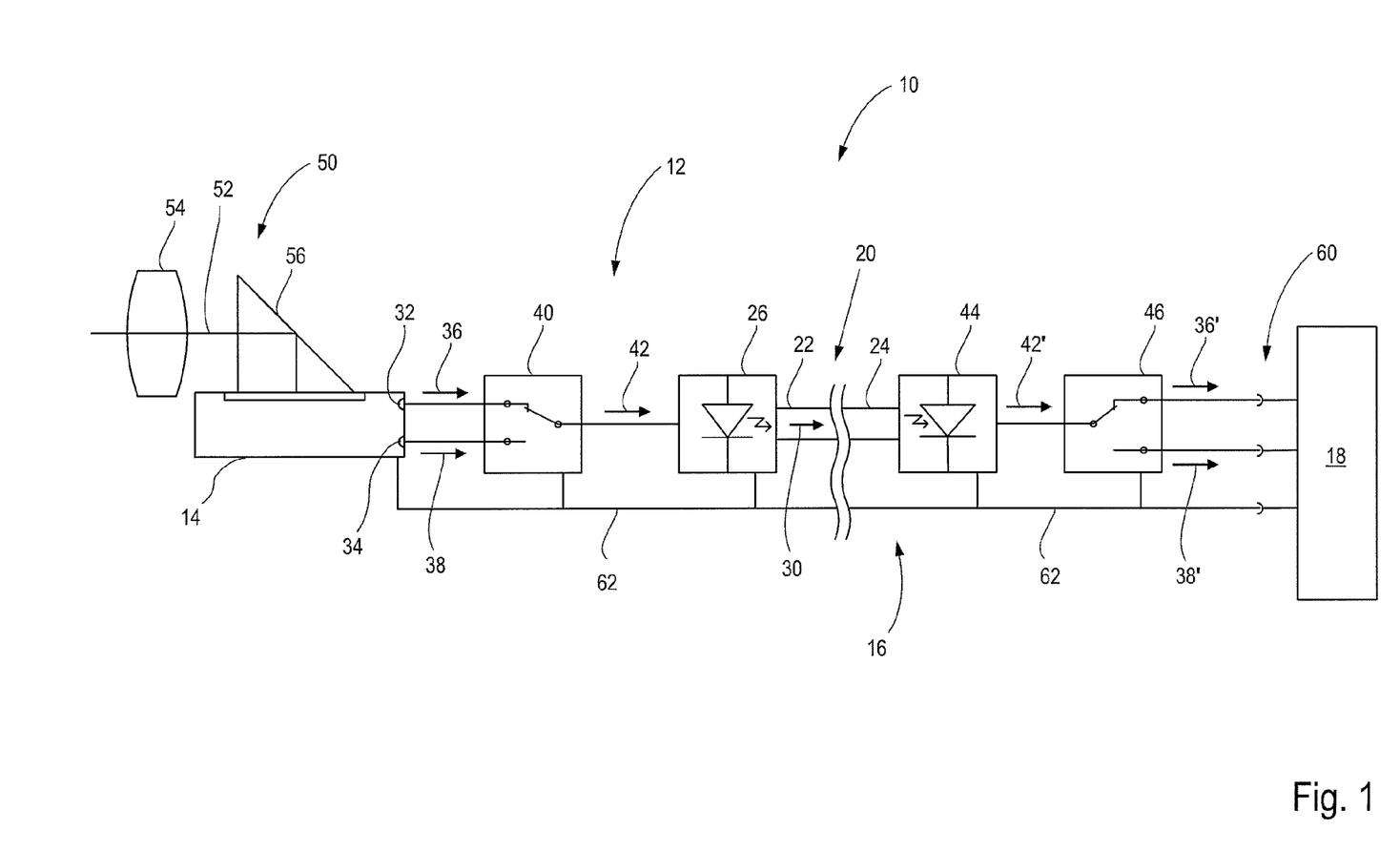
FIG. 1 a first embodiment of an endoscopic arrangement.

FIG. 1 shows an endoscopic arrangement 10 having a first distal end 12 at which an imaging device 14 is arranged, and comprising a first proximal end 16 for connection to an electrical unit 18. The arrangement 10 further comprises a data transmission element 20 which is embodied as a light guide. The data transmission element 20 has a second distal end and a second proximal end 24.

Preferably, the data transmission element 20 has a length of at least 3.3 ft (1 meter), more preferably at least 10 ft (3 m) and in particular at least 16 ft (5 m). In this embodiment the data transmission element 20 is embodied as a monomode-fiber. Also, in this embodiment, the imaging device 14 is configured to transmit the digital output signals 36, 38 according to the MIPI D-PHY or MIPI M-PHY specification. The same specification is applied to the signals 36', 38'.

The arrangement 10 further comprises an electro-optical converter 26 which is configured to convert the digital data generated by the imaging device 14 into an optical signal 30. The data transmission element 20 is optically coupled at its second distal end 22 to the electro-optical converter 26 for coupling the optical system 30 into the data transmission element 20.

The imaging device 14 comprises at least two data outputs 32, 34 each having a digital output signal 36, 38. In other words, the data outputs 32, 34 are each configured to output a digital output signal 36, 38. A first signal converter 40 is arranged between the imaging device 14 and the electro-optical converter 26, wherein the first signal converter 40 is embodied as a multiplexer in this embodiment. The first signal converter 40 is configured to combine the digital output signals 36, 38 into a digital combined output signal 42.

The imaging device 14 has a video resolution of more than 0.75 megapixel, preferably of more than 1.5 megapixel, more preferably of more than 2 megapixel (full-HD) and in particular of more than 8 megapixel (quad-HD) at an image frequency of preferably at least 15 images per second, more preferably at least 25 images per second and in particular of more than 30 images per second.

There have already been product announcements in quad-HD systems for CMOS-imaging sensors of a relatively small size and image resolutions above 8 megapixel, e.g. the imaging sensor OV10810 of Omnivision, St. Barbara, USA. These imaging sensors which could potentially be used in endoscopy require four times the transmission rate over full-HD.

For standard image frequencies of at least 25 images per second this results in very high transmission rates which may have several gigabit per second. These can be realized in an advantageous manner given the endoscopic boundary conditions requiring small diameters for the transmission system using the endoscopic arrangement disclosed.

A first opto-electrical converter 44 is arranged at the second proximal end 24 of the data transmission element 20. The opto-electrical converter 44 is configured to couple the optical system 30 out of the data transmission element 20 and to convert the optical signal 30 into digital data. The first opto-electrical converter 44 is connected to a second signal converter 46, which is configured to separate a digital combined output signal 42' in at least two digital output signals 36', 38'. It is noted that the opto-electrical converter 44 and the second signal converter 46 can be integrated into the electrical unit 18.

The identification of the signals as 36 and 36', 38 and 38', and 42 and 42', respectively, indicates that even though not the same physical signal is present due to the intermediate steps that take place during the signal transmission, the information that is sent from the distal side is contained in the information received at the proximal side.

The imaging device 14 has associated an optical arrangement 50 which provides an optical path with an optical axis 52 for light entering at the distal side to the imaging device 14. The optical arrangement 50 comprises a biconvex lens 54 and a prism 56. In this embodiment, the endoscopic arrangement 10 including the optical converter 44 and the second signal converter 46, which is embodied as a de-multiplexer, is connected via an electrical connector 60 to the electrical unit 18. As indicated in the Figure, the connection is releasable. The endoscopic arrangement 10 can therefore be replaced by another arrangement.

Further, an electric supply core 62 is shown which connects the electrical components at the distal side and at the proximal side with energy.

Figure 2:
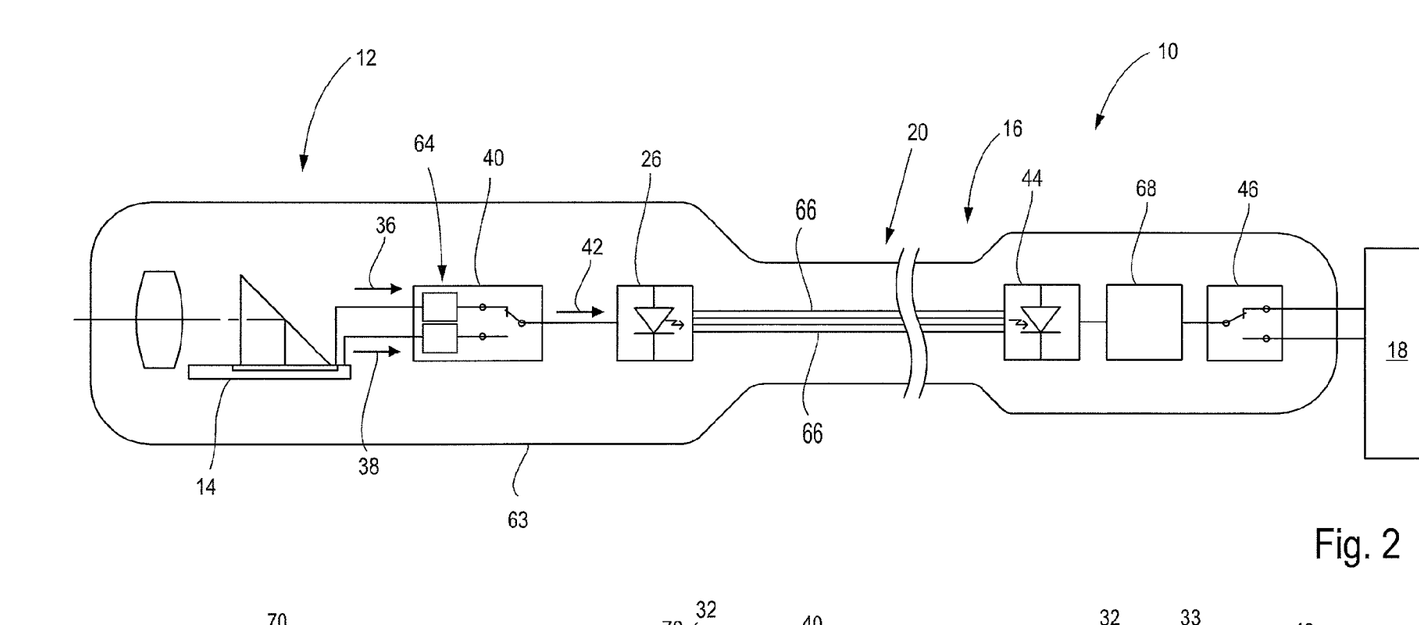
FIG. 2 a second embodiment of an endoscopic arrangement.

FIG. 2 shows a second embodiment of an endoscopic arrangement 10. The explanations regarding the functionality which have already been given in the context of the first embodiment will not be repeated and are considered applicable for this and the following Figures. Also, in order not to obscure the Figures, not all reference numerals are repeated. All reference numerals which have been introduced with the explanations in the context of the first embodiment continue to apply for this and the following Figures.

Different from FIG. 1 the endoscopic arrangement 10 according to the second embodiment is surrounded by a shell 63. The shell 63 protects the endoscopic arrangement from the outer environment, in particular from moisture.

The first signal converter 40 comprises, in this embodiment, a buffer memory 64 to temporarily store at least one of the digital output signals 36, 38—here: both digital output signals 36, 38. This allows for a very flexible combination of the digital combined output signal 42.

The data transmission element 20 comprises, in this embodiment, at least two fibers 66. The signal converter 40 is configured to couple the digital combined output signal 42 into the two fibers 66 of the data transmission element 20. The coupling into the two fibers 66 can be achieved by a light source in the electro-optical converter 26 which couples light into both fibers 66 and which is preferably embodied as a laser diode. In order to achieve an additional safety it is preferable that the coupling into the two fibers 66 is achieved via an individual light source for each fiber. This may offer a high safety for the data transmission.

In this context it is preferable, if the endoscopic arrangement 10 has a monitoring unit 68 which is configured to check the functionality of the optical transmission path. For example, if the transmission via one of the fibers 66 fails or, if the signals over the individual fibers 66 are evaluated separately, the received signals differ from one another, a notification can be provided that the endoscopic arrangement 10 is to be checked and, if necessary, is to be repaired or exchanged.

Figure 3A:
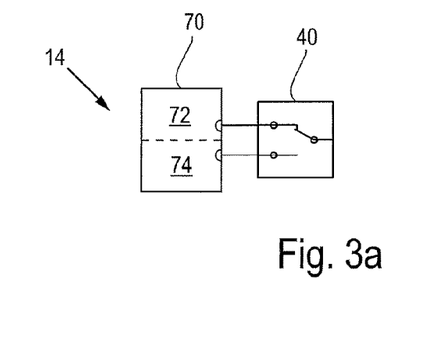
FIG. 3a a first embodiment of an imaging device.

FIG. 3a shows a first embodiment of an imaging device 14. An image sensor 70 is shown with a continuous imaging area, wherein a first part 72 and a second part 74 of the imaging area are read out separately via the data outputs 32 and 34.

Figure 3B:
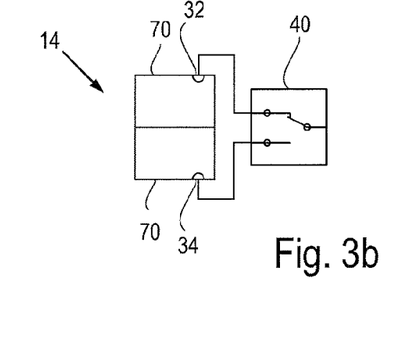
FIG. 3b a second embodiment of an imaging device.

FIG. 3b shows a second embodiment of an imaging device 14. Here, two image sensors 70 are provided which are each read out via a data output 32 and 34, respectively.

Figure 3C:
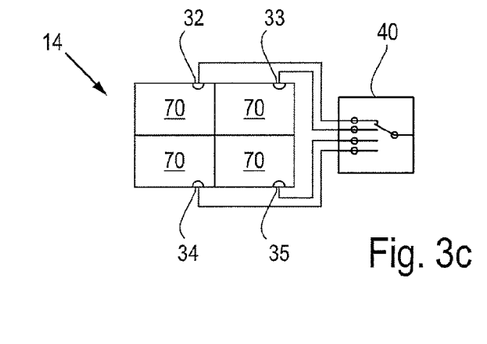
FIG. 3c a third embodiment of an imaging device.

FIG. 3c shows a third embodiment of an imaging device 14. Here, four imaging sensors 70 are provided which are each read out via a data output 32, 33, 34, 35, respectively.

Figure 4:
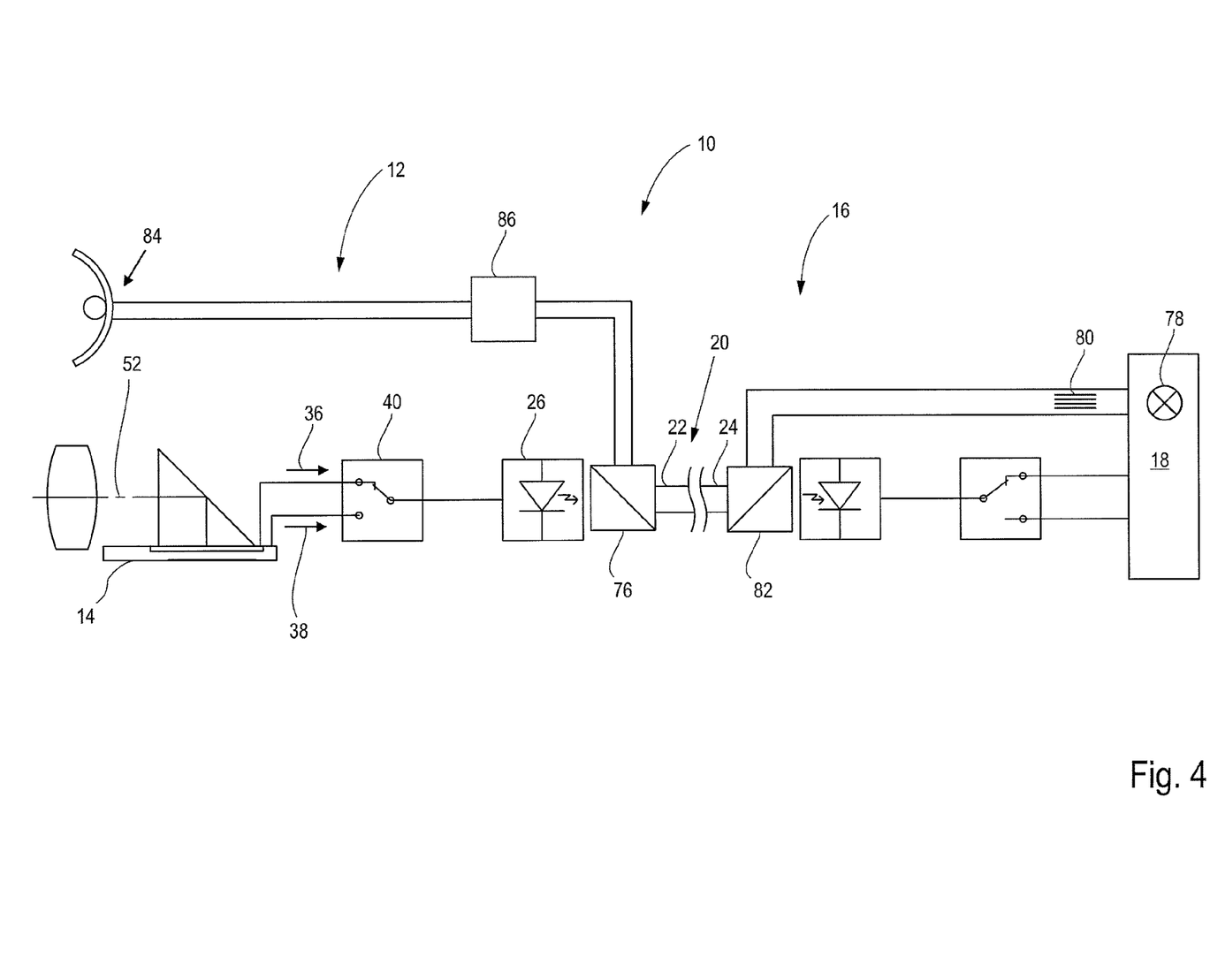
FIG. 4 a third embodiment of an endoscopic arrangement.

FIG. 4 shows a third embodiment of an endoscopic arrangement. Here, a spectral divider 76 is arranged between the electro-optical converter 26 and the second distal end 22 of the data transmission element 20. Further, at the first proximal end 24 of the endoscopic arrangement 10 a light source 78 is provided, here: integrated into the electrical unit 18, the light source 78 configured to couple light 80 at the first proximal end 24 into the data transmission element 20. The coupling is achieved via a further spectral divider 82.

At the first distal end 12 of the endoscopic arrangement 10 there is provided an exit 84 for visible light and a luminescence converter 86, wherein the luminescence converter 86 is configured to change light that is guided in the data transmission element 20 into white light and guide it to the exit 84.

In this third embodiment the light source 78 emits blue light, and the wave length for the transmission of the image data from the distal side to the proximal side is in the infrared, preferably near-infrared, range. This allows for a good separation of the different wave lengths by the spectral dividers 76, 82. At the spectral divider 76 the blue light is directed into the direction of the luminescence converter 86. There it is converted into white light, at least a light similar to white light, and then guided to the exit 84.

Figure 5:
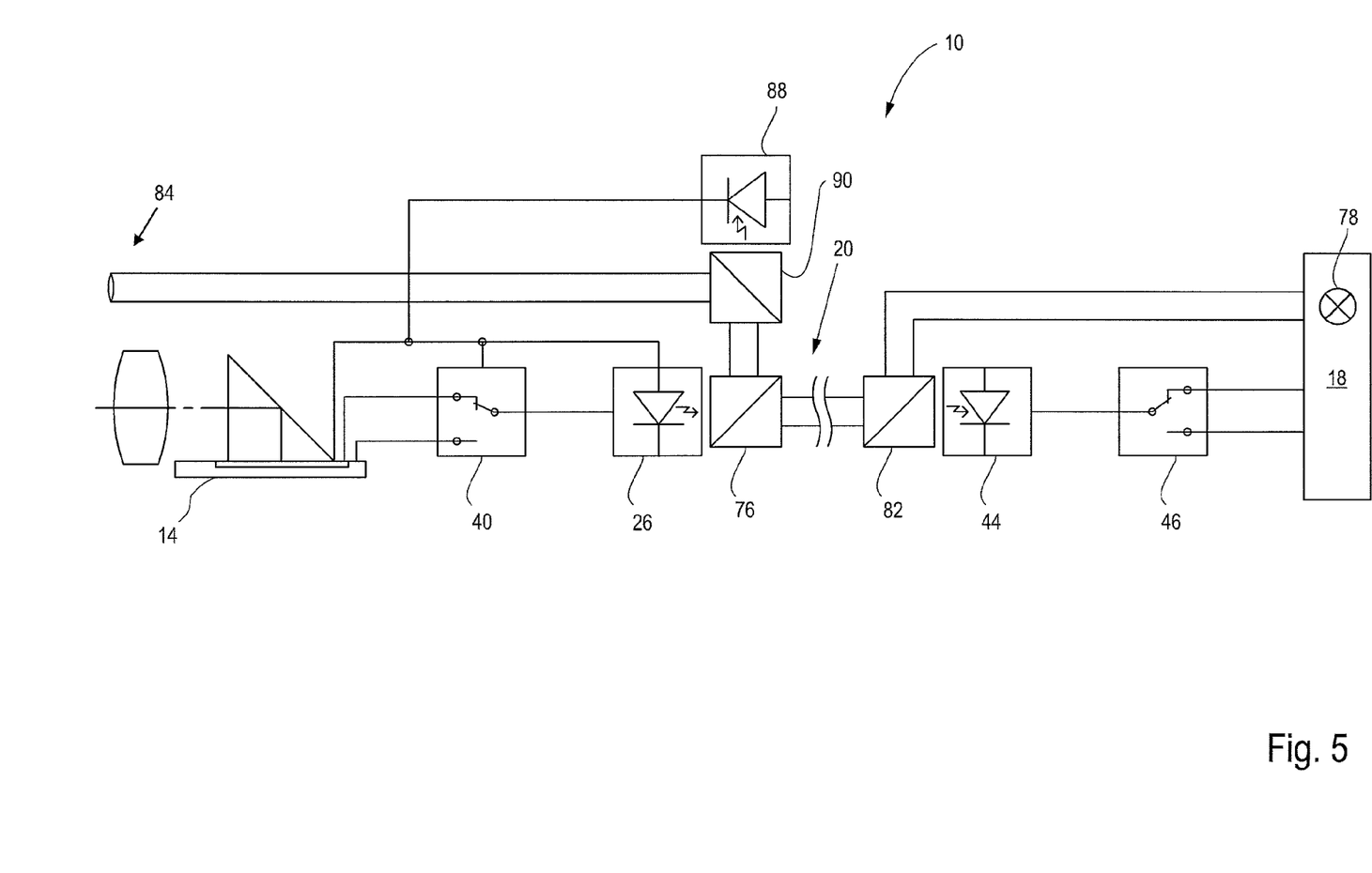
FIG. 5 a fourth embodiment of an endoscopic arrangement.

FIG. 5 shows a fourth embodiment of an endoscopic arrangement 10. Here, at the second distal end 22 of the endoscopic arrangement 10 a second opto-electrical converter 88 is arranged which is configured to convert light that is coupled at the proximal side into the data transmission element 20 into electrical energy. The light which is guided to the second opto-electrical converter 88 is coupled out via a partially transmissive mirror 90. The electrical energy is used for supplying the electrical components at the distal side with power, here, the imaging device 14, the signal converter 40 and the electro-optical converter 26.

Figures 6, 7A, 7B, 7C:
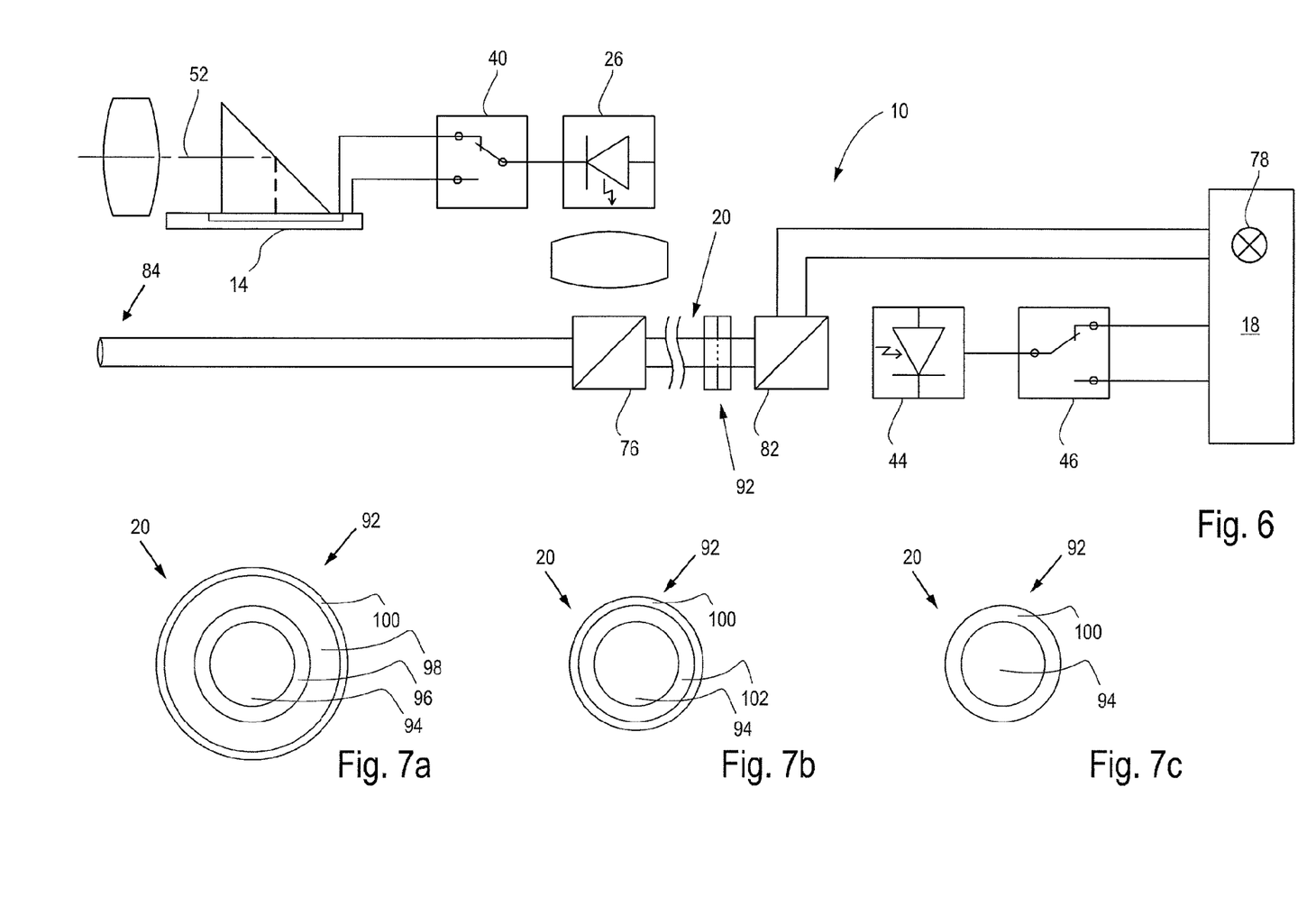
FIG. 6 a fifth embodiment of an endoscopic arrangement.
FIG. 7a a first embodiment of a separating section of an endoscopic arrangement.
FIG. 7b a second embodiment of a separating section of an endoscopic arrangement.
FIG. 7c a third embodiment of a separating section of an endoscopic arrangement.

FIG. 6 shows a fifth embodiment of an endoscopic arrangement. The data transmission element 20 comprises a separation section 92 at the first proximal end 16 of the endoscopic arrangement, the separation section 92 configured to allow a separation of the endoscopic arrangement 10 from a proximal electrical unit 18.

FIG. 7a shows a first embodiment in cross-section of a separation section 92. In the core of the data transmission element 20 a fiber is arranged for transmitting information from the distal side to the proximal side. The fiber 94 is surrounded by a reflecting layer 96. The reflecting layer 96 is surrounded by a further fiber or fibers 98, through which visible light is guided from the proximal side to the distal side. As explained above, it is also possible to guide the visible light through the fiber 94, if the fiber 94 is embodied as a multimode-fiber. The data transmission element 20 has a shell 100. This arrangement allows for a full rotation of the endoscopic arrangement relative to the electrical unit 18.

FIG. 7b shows a second embodiment of a separation section 92 where the light for the transmission of information and the visible light are transmitted in a fiber 94 having a reflecting layer. The fiber 94 is surrounded by an electrical core 102, which surrounds the shell 100. The electrical connection at the separation section 92 may be realized via a jumper ring. Therefore, also for this embodiment, a full rotation of the endoscopic arrangement 10 relative to the electrical unit 18 is possible.

FIG. 7c shows a third embodiment of a separation section 92. Here, the fiber 94 with a reflecting layer is surrounded by the shell 100. Such a separation section 92 is preferably used in the context of the embodiment shown in FIG. 5. The fiber 94 transmits the image information from the distal side to the proximal side and visible light from the proximal to the distal side. At the proximal side, the light is used as light for lighting as well as for generating electrical energy.

Figure 8:
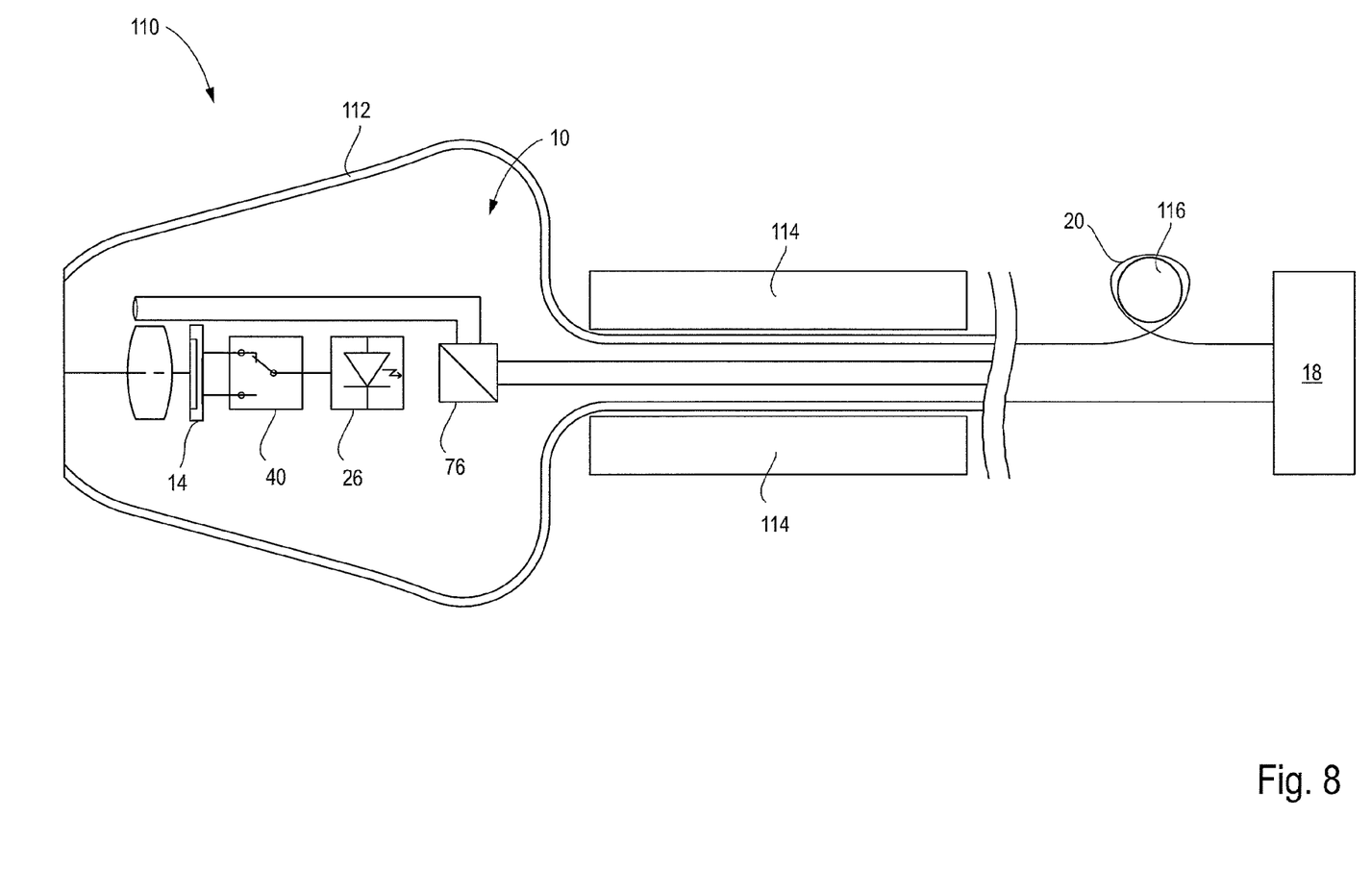
FIG. 8 a sixth embodiment of an endoscopic arrangement in an endoscopic capsule.

FIG. 8 shows an endoscopic capsule 110 with an endoscopic arrangement 10. The endoscopic arrangement 10 is enclosed in a capsule body 112, in particular the distal elements of the endoscopic arrangement are enclosed in the capsule body 112. Further, the endoscopic capsule 110 comprises an insertion system 114. The data transmission element 20 is wound as a roll on a roller 116 at the proximal side. The recovery of the optical signal is performed by the electrical unit 18.

Overall, there has been provided an endoscopic arrangement which is capable of a reliable transmission of video images at high or very high resolution despite the significant limitations in space regarding endoscopic applications.

What is claimed is:

1. An endoscopic arrangement comprising:
a first distal end;
an imaging device arranged at the first distal end, the imaging device having at least two digital data outputs, each of the at least two digital data outputs outputting a digital output signal;
a first signal converter combining the digital output signals from each of the at least two digital data outputs of the imaging device into a digital combined output signal;
a first proximal end for connection to a supply unit; and
a data transmission element embodied as a light guide and having a second distal end and a second proximal end,
the data transmission element comprising an electro-optical converter optically coupled to the data transmission element at the second distal end, the electro-optical converter configured to convert the digital combined output signal generated by the imaging device into an optical signal,
wherein the first signal converter is located between the imaging device and the electro-optical converter arranged at the first distal end of the endoscopic arrangement.

2. The endoscopic arrangement of claim 1, wherein the first signal converter comprises a buffer memory configured to temporarily store at least one of the digital output signals.

3. The endoscopic arrangement of claim 1, wherein the imaging device has a video resolution of more than 0.75 megapixel.

4. The endoscopic arrangement of claim 1, wherein a first opto-electrical converter is provided at the second proximal end of the data transmission element, the first opto-electrical converter configured to couple the optical signal out of the data transmission element and to convert the optical signal into digital data, and wherein a second signal converter is connected to the first opto-electrical converter, the second signal converter configured to separate a proximal digital combined output signal into at least two proximal digital output signals.

5. The endoscopic arrangement of claim 1, wherein a spectral divider is arranged between the electro-optical converter and the second distal end of the data transmission element.

6. The endoscopic arrangement of claim 1, wherein a second opto-electrical converter is arranged at the first distal end of the endoscopic arrangement, the second opto-electrical converter configured to convert light that is coupled into the data transmission element at the second proximal end into electrical energy.

7. The endoscopic arrangement of claim 1, wherein an exit for visible light and a luminescence converter are arranged at the first distal end of the endoscopic arrangement, wherein the luminescence converter is configured to convert light which is guided in the data transmission element into white light and to guide it towards the exit.

8. The endoscopic arrangement of claim 1, wherein a light source is provided at the first proximal end of the endoscopic arrangement, the light source configured to couple light at the first proximal end into the data transmission element.

9. The endoscopic arrangement of claim 1, wherein the data transmission element comprises a separation section at the first proximal end of the endoscopic arrangement, wherein the separation section is configured to allow a separation of the endoscopic arrangement from an electrical unit at a proximal side of the endoscopic arrangement.

10. The endoscopic arrangement of claim 9, wherein the first opto-electrical converter is couplable to the electrical unit via an electrical connector.

11. The endoscopic arrangement of claim 9, wherein the second signal converter is couplable to the electrical unit via an electrical connector.

12. The endoscopic arrangement of claim 1, wherein the data transmission element comprises a separation section at the first proximal end of the endoscopic arrangement, wherein the separation section is configured to allow a rotatable coupling of the endoscopic arrangement relative to an electrical unit at a proximal side of the endoscopic arrangement.

13. The endoscopic arrangement of claim 1, wherein the data transmission element is embodied as a monomode-fiber.

14. The endoscopic arrangement of claim 1, wherein the imaging device is configured to transmit the digital output signals according to the MIPI D-PHY specification.

15. The endoscopic arrangement of claim 1, wherein the imaging device is configured to transmit the digital output signals according to the MIPI M-PHY specification.

16. The endoscopic arrangement of claim 1, wherein the data transmission element comprises at least two fibers and wherein the electro-optical converter is configured to couple the digital combined output signal into the at least two fibers of the data transmission element.

17. An endoscopic capsule comprising the endoscopic arrangement of claim 1, wherein the capsule comprises an insertion system and a capsule body in which distal elements of the endoscopic arrangement are enclosed.

18. An endoscopic capsule comprising the endoscopic arrangement of claim 1, wherein the data transmission element is wound as a roll on a roller at the proximal side.

19. The endoscopic arrangement of claim 1, wherein the first signal converter is a multiplexer.

20. The endoscopic arrangement of claim 1, wherein the endoscopic arrangement is surrounded by a shell.

21. An endoscopic arrangement comprising:
a first distal end;
an imaging device arranged at the first distal end, the imaging device having at least two digital data outputs, each of the at least two digital data outputs outputting a digital output signal;
a first signal converter combining the digital output signals from each of the at least two digital data outputs of the imaging device into a digital combined output signal;
a first proximal end for connection to a supply unit; and
a data transmission element embodied as a light guide and having a second distal end and a second proximal end,
the data transmission element comprising an electro-optical converter optically coupled to the data transmission element at the second distal end, the electro-optical converter configured to convert the digital combined output signal generated by the imaging device into an optical signal,
wherein the first signal converter is located between the imaging device and the electro-optical converter arranged at the first distal end of the endoscopic arrangement,
wherein the data transmission element is embodied as a monomode-fiber and has a length of at least 1 meter,
wherein the imaging device is configured to transmit the digital output signals according to the MIPI D-PHY specification or MIPI M-PHY specification.

* * * * *